(12) United States Patent
Bayron et al.

(10) Patent No.: US 6,886,561 B2
(45) Date of Patent: May 3, 2005

(54) RESPIRATORY VALVE

(76) Inventors: Harry Bayron, #5 Milestone Way, West Palm Beach, FL (US) 33415; Neil Winthrop, 134 Sevilla Ave., Royal Palm Beach, FL (US) 33411

( * ) Notice: Subject to any disclaimer, the term of this patent is extended or adjusted under 35 U.S.C. 154(b) by 182 days.

(21) Appl. No.: 10/267,383

(22) Filed: Oct. 9, 2002

(65) Prior Publication Data

US 2004/0069308 A1 Apr. 15, 2004

(51) Int. Cl.[7] ................................................. A62B 9/02
(52) U.S. Cl. ........................... 128/205.24; 128/205.13; 128/207.14; 128/207.18
(58) Field of Search ..................... 128/200.24, 204.18, 128/205.13, 205.15, 205.17, 205.24, 207.14–207.18, 200.14, 203.11, 203.24, 203.28, 204.28, 205.16, 205.18, 205.19; 251/84, 284, 318, 321–325, 333, 336, 337, 359; 604/30, 33, 35, 540–544

(56) References Cited

U.S. PATENT DOCUMENTS

| | | |
|---|---|---|
| 3,780,736 A | 12/1973 | Chen |
| 4,351,328 A | 9/1982 | Bodai |
| 5,073,164 A * | 12/1991 | Hollister et al. ............... 604/43 |
| 5,207,641 A | 5/1993 | Allton |
| 5,309,902 A | 5/1994 | Kee et al. |
| 5,343,857 A | 9/1994 | Schneider et al. |
| 5,540,668 A * | 7/1996 | Wilson et al. ............... 604/248 |
| 5,746,199 A | 5/1998 | Bayron et al. |
| 6,098,622 A * | 8/2000 | Nobile et al. ........... 128/205.24 |
| 6,427,691 B1 * | 8/2002 | Jinotti ................... 128/205.24 |

* cited by examiner

*Primary Examiner*—Glenn K. Dawson
(74) *Attorney, Agent, or Firm*—McHale & Slavin

(57) ABSTRACT

A respiratory valve apparatus with a housing having a upper entry port and an opposite endotracheal tube connection port, along with a resuscitation bag connection port and an respirator connection port. The housing has an inner chamber. A reciprocating valve assembly fits within a chamber and slides between two positions whereby the entry, endotracheal, and respirator ports are open in one position, and the entry, endotracheal, and resuscitation ports are open in the second position. The valve assembly is a component of a surgical kit including a resuscitation bag, an endotracheal tube, and a suction catheter. A guide fixture can be attached to the entry port to help steer a catheter through the apparatus. An elongated protective bag can be sealably attached around the catheter to prevent external contact with the catheter surfaces when it is withdrawn.

14 Claims, 6 Drawing Sheets

RESPIRATORY VALVE

FIELD OF INVENTION

This invention relates to respiratory valves apparatus used in endotracheal medical procedures involving a respirator, a resuscitation bag, and a suction catheter. In particular, the present invention is a respiratory valve apparatus that facilitates rapid switching between a respirator, or breathing machine, and a resuscitation bag while maintaining ventilation functions and without losing positive end expiratory pressure (PEEP), the respiratory valve apparatus permitting the withdrawal and insertion of a catheter from a sanitary self-contained enclosure for endotracheal suctioning.

BACKGROUND OF THE INVENTION

Respiratory support systems are commonly used to support the respiratory system of a critically ill patient for maintaining optimal blood oxygen levels, as well as optimal carbon dioxide levels and acid base balance. Typically, a prior art respiratory support system includes a tracheal tube, positioned either directly through the nose or mouth into the trachea of a patient. A multi-ported manifold is connected to the endotracheal tube at one port position, and a source of breathable gas is connected at a second port. The respiratory support system assists the patient in maintaining adequate blood oxygenation levels without overtaxing the patient's heart and lungs.

While a patient is attached to the respiratory support system, it is periodically necessary to aspirate fluids and or secretions from the patient's trachea and lungs. In the past, in order to accomplish aspiration and positive pressure ventilation, it was necessary to disassemble part of the respiratory support system, either by removing the ventilator manifold or by opening a port thereof and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen can often drop and the carbon dioxide can change to unacceptable levels. Additionally, unless a sufficient positive end expiratory pressure (PEEP) level is maintained, then the lungs might collapse. This creates a dangerous condition for the patient because the lungs can be difficult, and sometimes impossible, to reinflate.

Patients may have fluid drawn from their lungs as often as six times a day and sometimes more, possibly over long periods of time. For this reason, it is critical to provide a respiratory device which will minimize patient discomfort. In addition, such a device could be widely used in treating pediatric patients, especially premature infants, as well as adults, who are subject to respiratory problems and may need frequent aspirations. As a result of the extremely large number of aspirations necessary on various patients in any period, it is important that the price of the respiratory device be as low as possible since vast numbers will be used. It is also important that the device be sufficiently inexpensive so that it may be discarded after a single use. Hence, it is desirable to simplify such devices and reduce the number of parts in order to reduce costs and increase reliability.

U.S. Pat. No. 5,746,199 to Bayron et al teaches a rotary valve with multiple ports, any two of which can be aligned with openings in the casing to provide through passages for delivering breathable gases to an endotracheal tube. The valve has a handle that cooperates with detents on the casing to secure the position of the rotary valve. However, any catheter inserted and removed through the endotracheal tube and valve ports that are connected with the ventilation ports provides a contact pathway for infectious organisms to the ventilators.

The manufacture of this rotary valve, as well as the other rotary valves mentioned here, requires precise control of the circular tolerances of the rotary valve and casing to prevent leakage around the valve. Such safety concerns increase the costs of manufacture and quality control measures.

Other prior art devices have attempted to maintain a continuous flow of oxygen from the respirator device through to the lungs, while allowing for insertion and retraction of the suction catheter. However, such devices fail to provide an operable system capable of performing both manual and machine assisted respiration without disconnecting the respirator. Manual respiration with a resuscitation bag during suction is a preferred method among many practitioners because it optimizes removal of fluids in the lungs while maintaining PEEP and maintaining cardiopulmonary and hemodynamic balance. U.S. Pat. No. 4,351,328 discloses a device for simultaneous respiration and endotracheal suctioning of a critically ill patient. This device requires a specialized sealing port for insertion and retraction of the suction catheter to maintain the integrity of the respiration system. While machine assisted respiration is occurring, no switchover to manual resuscitation methods is provided.

U.S. Pat. No. 5,343,857 discloses an accessory port capable of receiving a specially designed male adaptor on a suction catheter. The accessory port consists of a normally closed valve which is forced open by the male adaptor, and returns to its closed position upon retraction of the adaptor. The adaptor sealably interacts with the accessory port so as to inhibit pressure loss from the manifold. A similar device is disclosed in U.S. Pat. No. 5,309,902.

As detailed in the background discussions of these prior art disclosures, there are many difficulties associated with maintaining continuous pressure from the respiration supply device. More particularly, it is often desirable to be able to manually inflate the lungs with a resuscitation bag at different rates and different volumes in order to facilitate complete aspiration of mucous and liquid from the lungs. With the extra "hands-on" control offered by the resuscitation bag, a doctor or technician can simulate expectory coughing actions and the like through quick inflation and deflation bursts. Moreover, PEEP can be easily maintained with the resuscitation bag, while the suction catheter is repeatedly inserted and retracted from the lungs as needed.

Other interface devices require the respirator source to be disconnected in order to attach the desired resuscitation bag. Once aspiration is complete, this presents a problem with maintaining PEEP when the resuscitation bag is disconnected and the respirator source is reconnected. Even if performed in a timely and efficient manner, this switchover operation can jeopardize the patient's life if PEEP is not maintained. Hence, it is important to minimize this switchover time, while also providing for attachment of the resuscitation bag. Other devices remain connected to the respirator source and do not allow for use of a resuscitation bag.

U.S. Pat. No. 5,207,641 discloses a switching device with a rotary valve having aspiration, insufflation, and intermediate flushing positions. An oxygen port and suction port are included with a catheter port. These ports allow suction and insufflation to alternately occur through the continuously inserted catheter, without withdrawal of the catheter tube from the lungs. While providing a neutral valve position, this arrangement might still encounter problems such as blowback of mucous through the inserted catheter, and/or clogging of the valve parts by suctioned mucous.

U.S. Pat. No. 3,780,736 discloses a surgical valve assembly for urinary bladder irrigation and drainage. This valve has four ports and provides a core for interconnecting any two of the four ports. The core allows irrigation fluids to flow from one port to another, but the '736 device does not disclose a valve for introduction and withdrawal of a suction catheter through the device in either of two switched positions, and the '736 device does not disclose ports for receiving air from a respirator in one switched position or alternatively from a resuscitation bag in the other switched position.

Given the frequent insertion and withdrawal of the suction catheter, a protective bag, or sleeve, would also be a useful addition to existing suction catheter devices. This bag would prevent external contact with the catheter thereby maintaining a sterile device for reinsertion into the patient. U.S. Pat. No. 5,073,164 discloses a specialized catheter which incorporates a protective sleeve. A bag which can be sealably attached around any existing suction catheter would be even more versatile than the incorporated sleeve.

Accordingly, what is lacking in the art is a compact, inexpensive, improved, simplified respiratory device which can accommodate the introduction of a catheter into a patient's lungs separated from the respiratory valve while maintaining connection with an external respirator source, and which will subsequently allow uninterrupted respiratory switchover to a resuscitation bag to maintain optimal ventilation.

SUMMARY OF THE INVENTION

The present invention provides a respiratory valve apparatus with an elongated housing having an a ventilating valve structure separated from an aspiration port. The ventilating valve switches between a manual resuscitation bag port and a ventilator port. A patient can thereby receive continuous support from a respirator or an attached resuscitation bag, depending upon the position of the valve. By providing an efficient switchover between the respirator and resuscitation bag, a patient can be treated in such a manner without having to disconnect the respirator support system to thereby connect the resuscitation bag. This prevents the loss of positive end expiratory pressure (PEEP) in the lungs and guards against lung collapse and hemodynamic compromise. The apparatus provides a separate port with a sealing orifice for insertion and retraction of a catheter into the endotracheal tube to prevent contact contamination of the valve.

Additional features include a hingably attached cover for the resuscitation bag port when a resuscitation bag is not attached. A hingably covered or sealable port for a catheter suitable for injection of saline or aspiration.

It is therefore an object of the present invention to provide a respiratory valve apparatus which can switch between an attached external respirator support system and an attached resuscitation bag, and can accommodate insertion of a suction catheter through the apparatus when placed in either switched position.

It is a related object of the present invention to provide a respiratory valve apparatus having a housing with a suction catheter entry port, a endotracheal tube connection port, a respirator connection port, and a resuscitation bag connection port.

It is still another object of the present invention to provide an inner reciprocating valve assembly contained within the apparatus which closes the respirator port and opens the resuscitation bag port in one position and opens the respirator port and closes the resuscitation bag port in another position.

It is yet another object of the present invention to provide a separate sealable entry port in the apparatus which seals upon withdrawal of the catheter.

It is a further object of the present invention to provide a spring bias in the reciprocating valve.

It is another object of the present invention to provide a universal adapter to connect to different conventional resuscitation bags.

It is still another object of the present invention to provide a hingably attached cover for the resuscitation bag port for sealably covering the port when a bag is not attached.

It is yet another object of the present invention to provide a hingably covered or sealable saline port in the housing assembly for injecting saline to clean the valve assembly parts.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention is described in terms of a several embodiments, it will be readily apparent to those skilled in this art that other various modifications, rearrangements and substitutions can be made without departing from the spirit of the invention. The scope of the invention is defined by the claims appended hereto.

Figure 1:
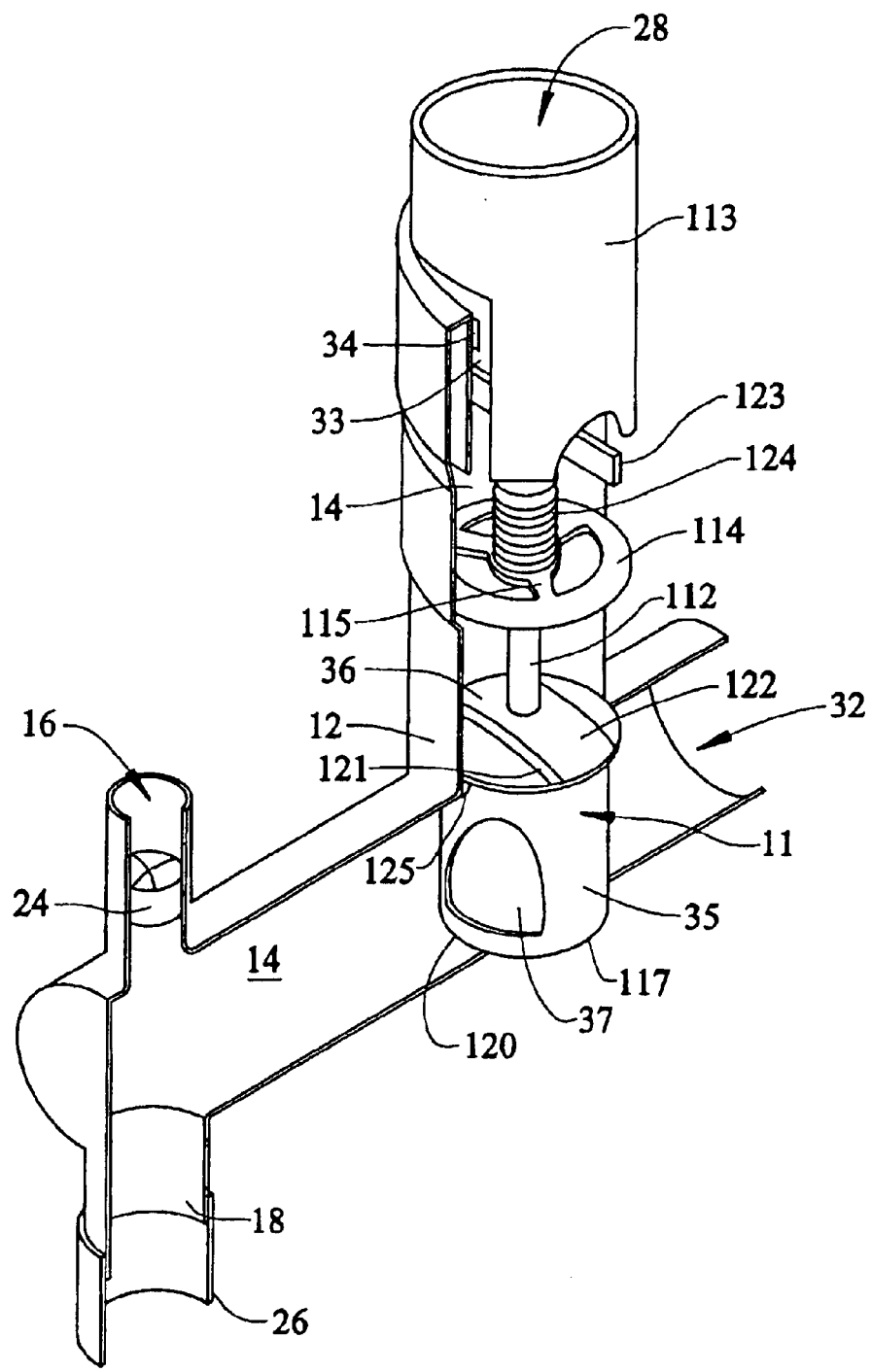
FIG. 1 shows a partial cross section of one embodiment of the respiratory valve assembly of this invention with the respirator port closed and the resuscitation bag port open.
Figure 2:
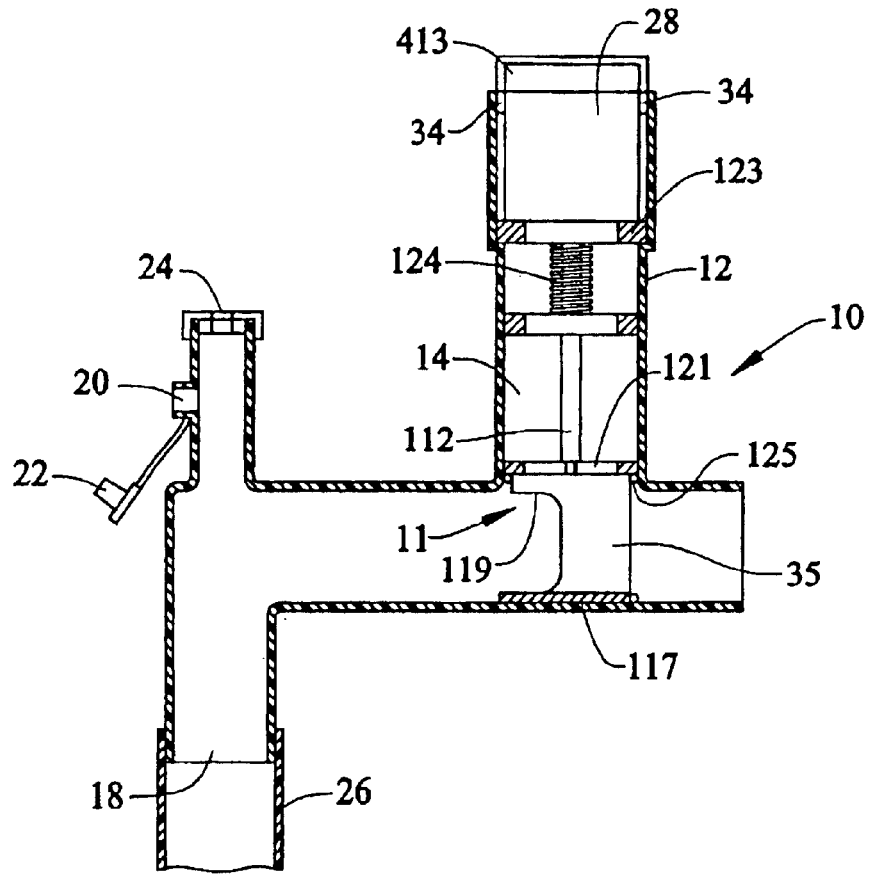
FIG. 2 shows an a partial cross section as in FIG. 1 with the respirator port closed.

Referring now to FIGS. 1 and 2, the assembly has a housing 12 and an inner chamber 14. The housing 12 includes an upper access port which is a suction catheter entry port 16 located on the top and a endotracheal tube connection port 18 located on the bottom. The entry port 16 has a flexible orifice 24 covering the top and may include a saline injection port 20, shown in FIG. 3, which can be covered by a hingably attached plug 22. Port 20 might alternatively use a sealable orifice. The sealable orifice may be closed with a cap of resilient material having diametrical cuts forming openable flaps. Alternatively, the aspiration port 16 may be used for administering a saline solution. An endotracheal tube 26 can be removably attached to the endotracheal connection port 18.

In the embodiment shown in FIGS. 1–2, the housing 12 is an elongated L-shaped tubular structure with the respirator port 32 at one end and the endotracheal connection port 18 at the other end. The resuscitation bag port 28 extends from the shaft of the L-shaped housing.

The valve 11 is a hollow cylinder 35 with an open top 36, a closed bottom, and an opening 37 in the side wall. The opening 37 is aligned with the endotracheal tube port 18 so that air from the resuscitation bag flows through the resuscitation bag port, through the cylinder and into the endotracheal tube port while the remainder of the cylinder wall blocks the respirator port. The reciprocating valve 11 slides partially within the resuscitation bag port 28 and the inner chamber 14 intermediate the ends of the L-shaped housing. The reciprocating valve 11 and the resuscitation bag port are normal to the respirator valve port 32. The valve 11 is moved by the universal resuscitation bag adapter 113 in the port 28. As the valve moves, it opens the resuscitation bag port 28 and closes the respirator port 32. The valve 11 has a valve stem 112 that telescopes through a valve spacer 114. The universal resuscitation bag adapter 113 serves to connect different resuscitation bags to the respiratory bag. In the event the respiratory valve is supplied as part of a kit, including a resuscitation bag, the adapter may not be present.

Figure 2A:
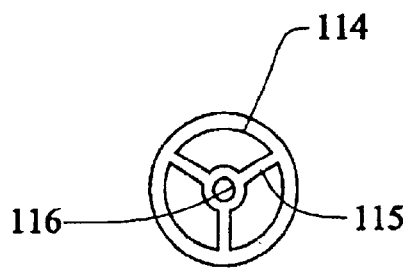
FIG. 2A shows a plan view of a guide shown in FIG. 2.

The spacer 114 has an outer ring with the circumference fixed to the resuscitation bag port wall. The spacer 114 is a stop for the spring 124. The ring may have spokes 115 and a hub 116, as shown in FIG. 2A. The hub 116 is of such diameter to permit the sliding movement of the valve stem 112 therethrough. The movement of the valve stem 112 through hub 116 and the circumferential sliding contact between valve 11 and the resuscitation bag port acts as a valve guide.

Figure 1A:
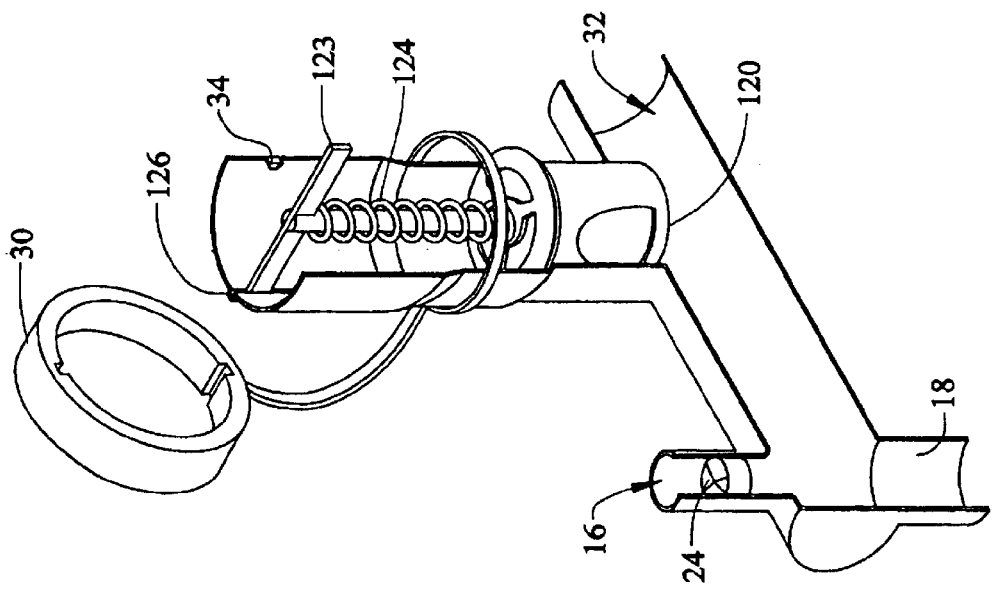
FIG. 1A shows a partial perspective view of the respiratory valve assembly of FIG. 1 with the respirator port open.
Figure 2B:
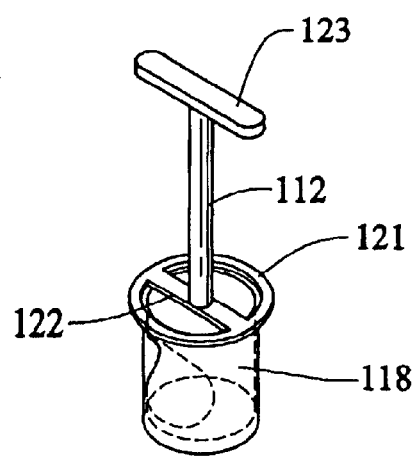
FIG. 2B shows a perspective of the cylinder valve shown in FIG. 2.

The valve 11 has a circular solid valve bottom face 117 of a diameter to close the valve seat 125 at the inner end of the resuscitation bag port 28, as shown in FIG. 1. The circular face 117 also forms one end of the cylindrical sleeve 35. The length and diameter of the sleeve 35 is such to close the respiratory port, as shown in FIG. 2. As shown in FIGS. 1 and 1A, the solid plate and the sleeve are stopped and sealed by the circular valve seat 120. As shown in FIG. 2B, the upper edge of the sleeve 35 is formed with a ring 121 which slides along the inside of the resuscitation bag port to further stabilize the reciprocation of the valve 11. The ring supports the end of the valve stem with chord bars 122. The ring 121 may also be similar in form to the valve spacer 114. The upper end of the valve stem 112 has a retainer 123. The retainer 123 may be in the form of a cross bar, as shown, or a perforated ring to allow air passage.

The resuscitation bag adapter will engage the retainer 123, such as shown in FIG. 1. A coil spring 124 is mounted about the valve stem and held in place by the retainer 123. The other end of the coil spring rests on the valve spacer 114. In this manner, the spring is compressed as the resuscitation bag adapter 113 moves the valve to close the ventilator port. The retainer 123 slidably contacts the inside of the resuscitation bag port. The inner wall of the resuscitation bag port also has two opposing longitudinal grooves 126. The ends of the retainer 123 slide in the grooves 126 in response to pressure from the adapter 113. The grooves maintain alignment of the opening 37 in the valve cylinder with the endotracheal tube port 18. The enlarged portion may or may not be present in order to accommodate the conventional resuscitation bag fittings.

As shown in FIG. 1, the tubular adapter 113 has opposite bayonet slots 33 in the side wall. The slots cooperate with opposing lugs 34 on the resuscitation bag port wall to guide movement of the adapter and lock the port open while the bag is being used.

Figure 3:
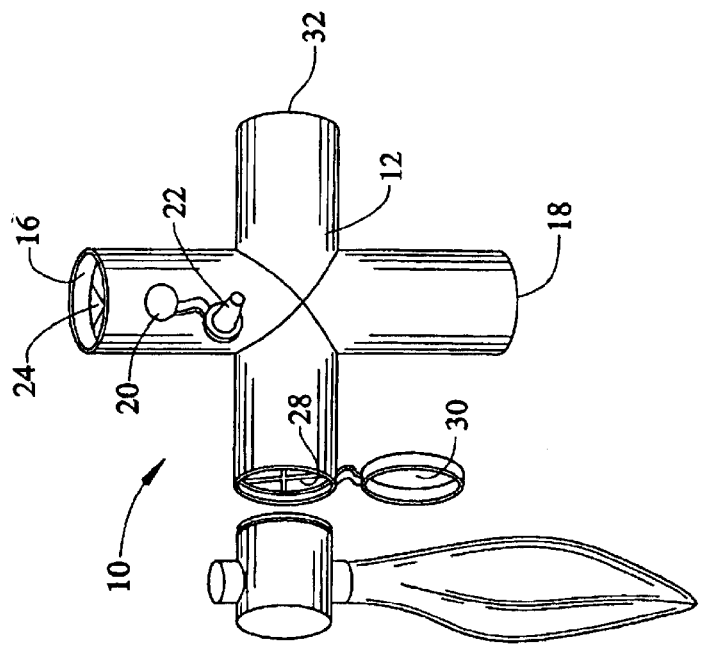
FIG. 3 shows a perspective of another embodiment of the respiratory valve assembly of this invention with a resuscitation bag.

Therefore, as shown in FIG. 1, with the respirator valve port 32 closed, the patient can receive manual resuscitation bag breathing augmentation through the inner chamber of the valve assembly. A resuscitation bag, as shown in FIG. 3, may be connected to the universal resuscitation bag adapter and the valve assembly will automatically move the valve to close the respirator port and open the resuscitation bag port, as shown in FIG. 1A. When the bag is disconnected, the adapter is rotated to unlock the bayonet fitting and the valve assembly automatically re-establishes the airway between the respirator and the patient.

A connection to the patient is located at the bottom of the L-shaped valve assembly, usually by an endotracheal tube attached to the valve assembly. As shown in FIGS. 1 and 2, the aspirator port 16 is in line with the endotracheal port 18. This suction tube port is normally closed either by a removable cap or a resealing entry 24. The suction tube is linearly displaced from the reciprocating valve, the resuscitation bag and the respirator to avoid direct contact with any contamination in the suction tube.

Figure 4:
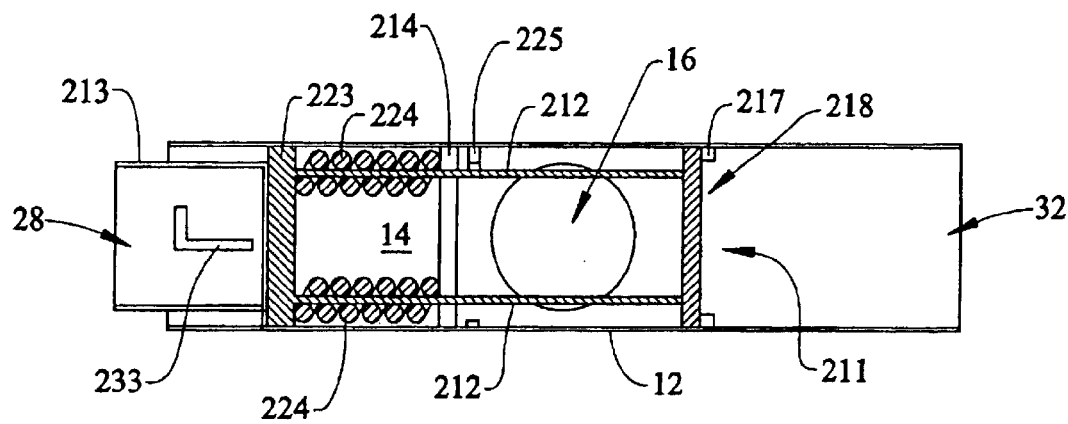
FIG. 4 shows a top plan view of the respiratory valve assembly of FIG. 3, partially in section.
Figure 5:
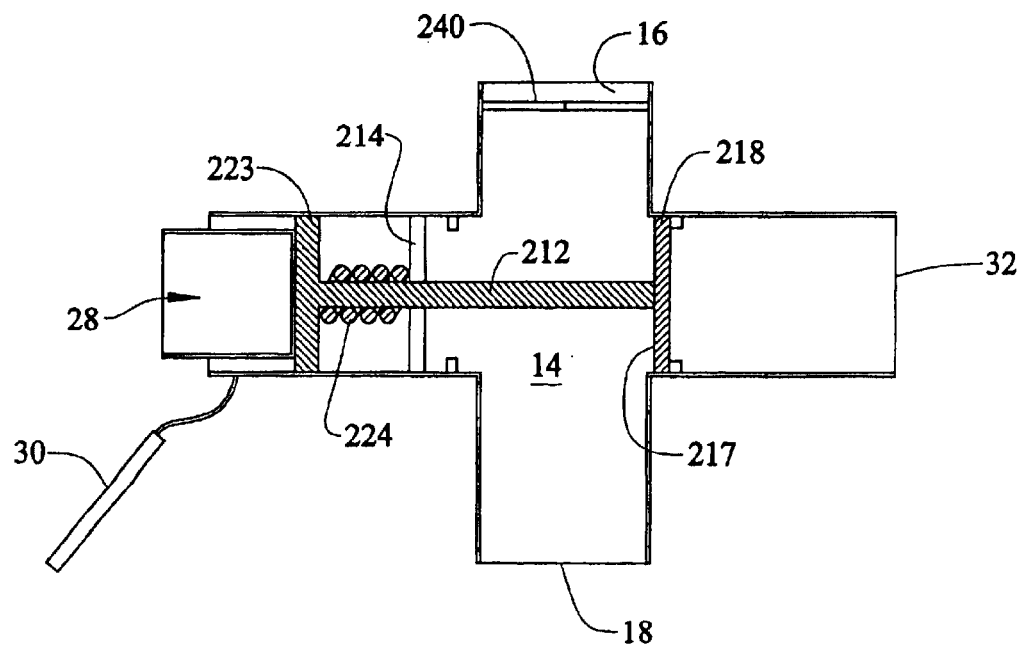
FIG. 5 shows a side view of the valve assembly of FIG. 4, partially in section.

In the embodiment shown in FIGS. 3–5, a cruciform valve assembly has a resuscitation bag attachment port 28 extending out one side, oriented approximately 90 degrees from the entry port 16 and endotracheal tube connection port 18. This port 28 can be sealably covered by a hingably attached cover 30. On the opposite side of the bag attachment port 28 is a respirator attachment port 32 for attaching an external respirator device.

In this embodiment, the linear displacement of the suction tube from the valve is accomplished by a bifurcated valve stem 212. As shown, a valve spring 224 is coiled about each element of the split stem with one end contacting a retainer 223 on each split. Alternatively, a single coil spring could encircle the bifurcated valve stem. The retainer may be a cross bar, as shown in FIG. 1 or a perforated disk. The other end of the coil spring contacts the back side of the resuscitation bag port valve spacer 214.

The spacer 214 is fixed about its circumference in the resuscitation bag port 28. The spacer 214 is perforated, as is spacer 114, but has two apertures for sliding engagement with the bifurcated valve stem 212. Each spring 224 rests on the spacer 214 and is compressed by the valve retainer 223 as the valve reciprocates toward the respirator port.

The valve 211 is a solid disk and has a diameter very close to the diameter of the resuscitation bag port and the respirator port to form an edge seal with each port when seated therein. Alternatively, each port may have an internal valve seat to contact the opposite faces of the circular valve, as shown in FIGS. 4 and 5. These valve seats also serve as stops for the reciprocating movement of the valve. One face of the valve closes the resuscitation bag port 28 at seat 225 and the other face 218 of the valve face seats in the respirator port 32 at valve seat 217.

Figure 9:
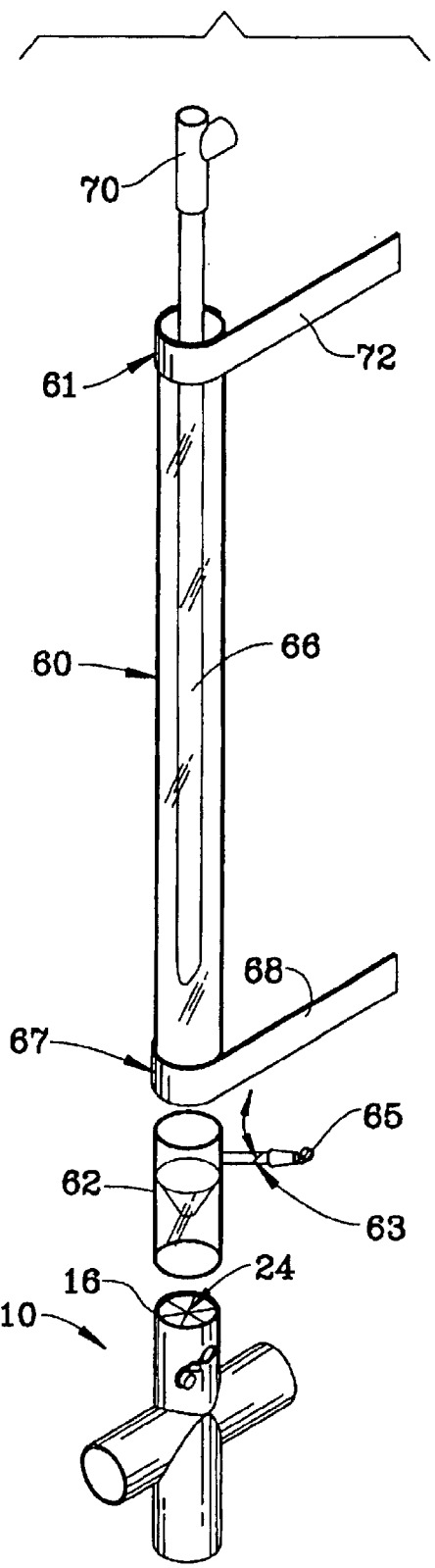
FIG. 9 shows an exploded perspective of the respiratory valve and catheter.
Figure 10:
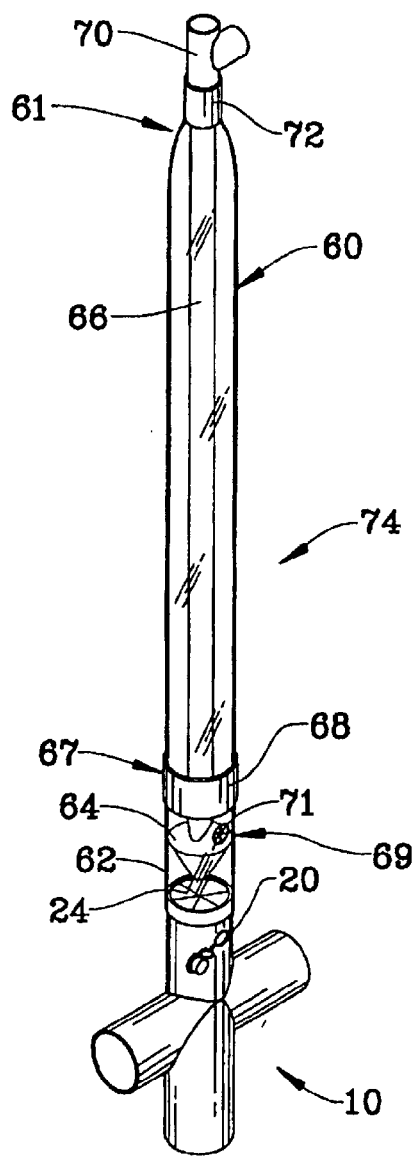
FIG. 10 shows a perspective of the respiratory valve with catheter and bag attached.

In this manner, the valve stem is housed in the resuscitation bag port while that port is closed. A suction tube may be inserted directly through the aspiration port into the endtracheal connection port without contacting either valve, as shown in FIGS. 9–10. With the respirator port closed by the valve, an aspirator tube may pass between the elements of the split valve stem 212. To provide better reciprocatory support, each element of the split valve stem may be formed with a semicircular outer surface with the same diameter as the valve 218.

Figure 6:
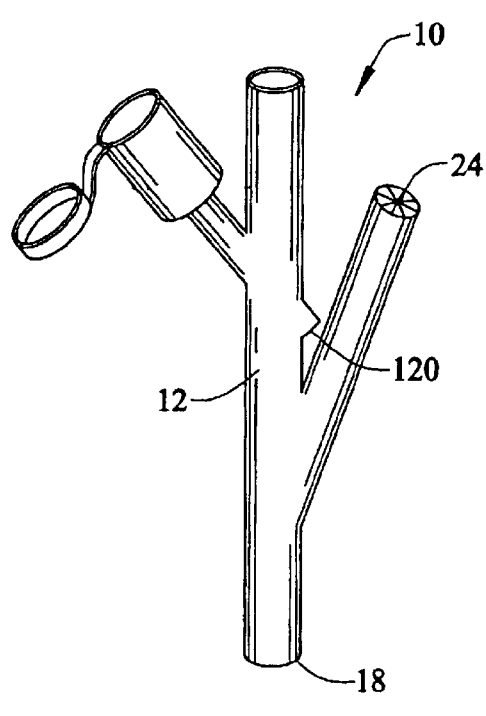
FIG. 6 shows a perspective of another embodiment of the respiratory valve assembly of this invention.
Figure 7:
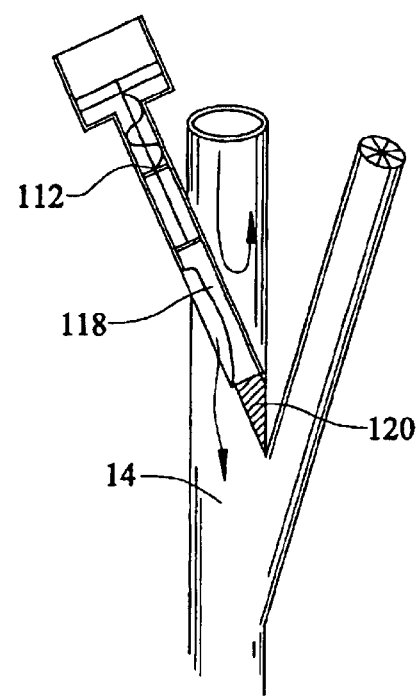
FIG. 7 shows a cross section of the valve assembly of FIG. 6 with the respirator port closed.
Figure 8:
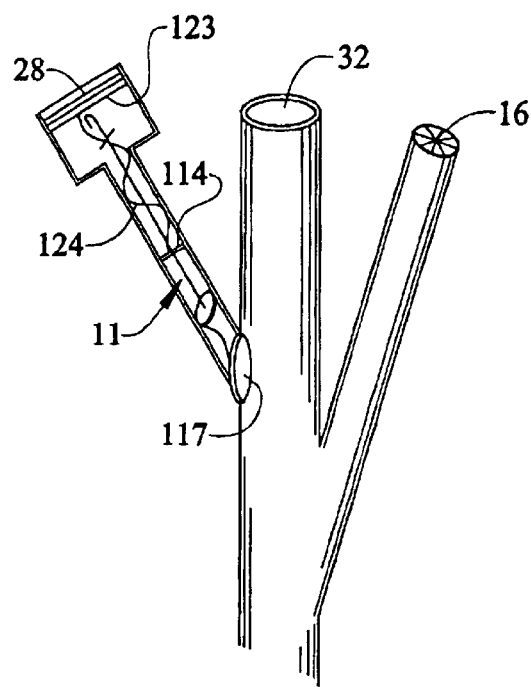
FIG. 8 shows a cross section of FIG. 6 with the respirator port open.

The embodiment shown in FIGS. 6–8 provides a smaller profile for the valve assembly. This smaller embodiment would be extremely useful when working with infants and children. In this embodiment, the operation and structure of valve 11 is the same as the L-shaped valve assembly of FIGS. 1–2. The angular relations between the ports have been modified to reduce the overall size of the device. The suction catheter entry port 16 enters the housing 12 downstream from the resuscitation bag port and valve 11 to provide the linear displacement between the suction catheter and the valve. In all other respects, the valve assembly and operation are the same.

In each of the embodiments, the inner chamber 14 provides a conduit between the entry port 16 and endotracheal tube connection port 18 whereby a suction catheter can be inserted through the valve assembly 10. A resuscitation bag, not shown, can be attached to the resuscitation bag port 28. With the endotracheal tube 26 attached to the connection port 18, the respiratory valve assembly 10 could be positioned over a patient's mouth with the endotracheal tube extending into the patient. A catheter could be inserted through the inner chamber and the resuscitation bag could be used to manually provide volumetric units of air into the patient's lungs. By skillfully combining the manual inflation actions with the suction catheter procedure, optimum clearing of the lungs can be accomplished. At which time the suction catheter may be removed from the assembly.

When the bag is removed from the respiratory valve, the reciprocating valve 11 closes resuscitation bag port and opens the respirator attachment port 32 so that the respirator connection will now be breathably connected to the patient without loss of PEEP in the patient's lungs. The suction catheter can then be reinserted and withdrawn as needed through the assembly 10.

FIG. 6 illustrates a valve seat 120 matching the circumference of the internal valve 11 extending through the respirator port. As an alternative, the interior wall of the respirator port may be molded to form a seat for the bottom of the valve 11, as shown in FIGS. 7–8. This same structure may be used in the respiratory valve shown in FIGS. 1–2.

Referring now to FIG. 9, a perspective view of the respiratory valve assembly 10 is shown with an exploded view of the additional bag-like attachment 60 and an attachment fixture 62. The attachment fixture 62 is tubular in shape and removably attaches, via snug frictional contact or otherwise, with the catheter entry port 16. While the preferred embodiment would likely be constructed of opaque plastic, a transparent version of the attachment fixture 62 shows an inner conical guide 64 which steers an inserted catheter down through the center portion of the orifice 24. This eases catheter insertion through the orifice 24 because the center part of the orifice is more flexible and less resistant than the edges. The bag-like attachment 60 is threaded over the suction catheter 66 and the bottom end 67 of the bag is secured around the fixture 62 with a strip of seal forming adhesive tape 68, or other such materials. The upper end 61 of the bag 60 is secured around the upper attachment fixture 70 by another strip of seal forming adhesive tape 72. Also shown is a saline adaptor port 63 for flushing out the system which extends outwards for convenient access and has a hingably attached cover 65. In lieu of, or in addition to, the hingably attached cover 65, the port 63 might include a bendable, or hingable flap 75 within the extension tube which would allow for injection of saline in one direction, and which would spring back into position to prevent further escape of gas and/or fluids when the saline injection device is withdrawn.

Referring now to FIG. 10, a perspective view of the assembled device 74 is shown. The guide fixture 62 fits over the entry port 16 so as not to block the saline injection port 20. The adhesive tape strip 68 wraps around and secures the bottom bag end 67 to the fixture 62. The conical guide section 64 is then placed over the center of the orifice 24. The upper end 61 of the bag 60 is sealably constricted around the upper attachment fixture 70 via the adhesive tape strip 72. This guide fixture 62 shows an alternative saline port 69 which is located flush on the side of the fixture 62 and which uses a sealable orifice 71. Any saline port configuration can be used as appropriate.

The respiratory valve assembly, a resuscitation bag, an endotracheal tube, and a suction tube may be supplied as a surgical tray or kit. This organization presents the physician and nurses with all the equipment to perform a complete procedure. All of the components are sized to securely fit together and are located in the same kit.

It is to be understood that while certain forms of the invention are illustrated, it is not to be limited to the specific forms or arrangements of parts herein described and shown. It will be apparent to those skilled in the art that various changes may be made without departing from the scope of the invention and the invention is not to be considered limited to what is shown in the drawings and descriptions.

What is claimed is:

1. A respiratory valve apparatus comprising:

a housing having an inner chamber connected to an access port, an endotracheal tube connection port, a respirator connection port and a resuscitation bag connection port;

said respirator connection port and said resuscitation bag port each having a valve seat inside said inner chamber;

a reciprocating valve assembly which slidably fits inside said inner chamber, said assembly having a valve connected to a valve stem, said assembly closing said resuscitation bag connection port with said valve engaging said valve seat in said resuscitation bag port and opening said respirator connection port in a first position;

said assembly adapted to reciprocate to open said resuscitation bag connection port and close said respirator connection port with said valve engaging said valve seat in said respirator connection port in a second position;

a channel being aligned with said access port and said endotracheal tube connection port;

wherein a suction catheter can be inserted through said channel in said first and second valve assembly positions.

2. The respiratory valve apparatus of claim 1, wherein said valve assembly includes a spring means biasing said assembly to said first position.

3. The respiratory valve apparatus of claim 1, wherein said valve stem includes a retainer, a valve spacer fixed in said resuscitation bag port, means for biasing including a coil spring, one end of said coil spring contacting said retainer, the other end of said coil spring contacting said valve spacer whereby said spring is compressed as said valve moves from said resuscitation bag port toward said respirator port.

4. The respiratory valve apparatus of claim 1, wherein said access port includes a sealable orifice adapted for entry of said suction catheter and which seals upon retraction of said catheter.

5. The respiratory valve apparatus of claim 1, wherein said resuscitation bag connection port includes a hingably attached port cover.

6. The respiratory valve apparatus of claim 1, wherein said housing includes a saline injection port with a sealable orifice.

7. The respiratory valve apparatus of claim 6, wherein said saline injection port comprises a hingably attached port plug.

8. The respiratory valve apparatus of claim 1, which further includes a kit having a resuscitation bag adapted to securely connect with said resuscitation bag connection port, an endotracheal tube adapted to securely connect with said endotracheal tube connection port and a suction tube adapted to pass through said access port into said endotracheal tube.

9. The respiratory valve apparatus of claim 8, which further includes an elongated protective bag with an upper and lower end, and an entry port guiding fixture, said guiding fixture fitting onto said access port and containing a conically shaped inner surface for guiding said catheter into said apparatus, said lower end of said protective bag being sealably attached to said guiding fixture, and said upper end of said protective bag being sealably attached to an upper end of said catheter.

10. The respiratory valve apparatus of claim 9, wherein said bag is sealably attached using adhesive tape.

11. The respiratory valve apparatus of claim 1, wherein said reciprocating valve includes a hollow cylindrical sidewall with one open end and another closed end, said valve stem connected to said open end, said cylindrical wall having a discrete opening therein aligned with said endotracheal tube connection port whereby a pathway is formed through said open end and said opening, said closed end blocking said resuscitation bag port in said first position.

12. A respiratory valve apparatus of claim 11, wherein said sidewall of said reciprocating valve blocks said respirator port in said second position.

13. A respiratory valve apparatus of claim 1, wherein said housing is approximately cruciform, said resuscitation bag port and said respirator port are off set approximately 180 degrees and said reciprocating valve includes a solid disk.

14. A respiratory valve apparatus of claim 13, wherein said access port is between said resuscitation bag port and said respirator port, said valve stem is bifurcated whereby a catheter may pass through said access port and said endotracheal tube connection port while said valve is in said second position.

* * * * *